US011872352B2

(12) United States Patent
Abbas

(10) Patent No.: US 11,872,352 B2
(45) Date of Patent: Jan. 16, 2024

(54) MULTI-FUNCTION HYPOSPADIAS CATHETER

(71) Applicant: HAMAD MEDICAL CORPORATION, Doha (QA)

(72) Inventor: Tariq Osman Saeed Abbas, Doha (QA)

(73) Assignee: HAMAD MEDICAL CORPORATION, Doha (QA)

( * ) Notice: Subject to any disclaimer, the term of this patent is extended or adjusted under 35 U.S.C. 154(b) by 637 days.

(21) Appl. No.: 16/979,055

(22) PCT Filed: Mar. 8, 2019

(86) PCT No.: PCT/QA2019/050004
§ 371 (c)(1),
(2) Date: Sep. 8, 2020

(87) PCT Pub. No.: WO2019/177478
PCT Pub. Date: Sep. 19, 2019

(65) Prior Publication Data
US 2020/0406005 A1     Dec. 31, 2020

Related U.S. Application Data

(60) Provisional application No. 62/642,345, filed on Mar. 13, 2018.

(51) Int. Cl.
*A61M 25/00*      (2006.01)
*A61M 25/04*      (2006.01)
(Continued)

(52) U.S. Cl.
CPC .... *A61M 25/0017* (2013.01); *A61M 25/0028* (2013.01); *A61M 25/0045* (2013.01);
(Continued)

(58) Field of Classification Search
CPC .......... A61M 25/0017; A61M 25/1002; A61M 25/10; A61M 25/0041; A61M 2025/0063;
(Continued)

(56) References Cited

U.S. PATENT DOCUMENTS

| 3,811,448 A | 5/1974 | Morton |
| 3,825,013 A * | 7/1974 | Craven ................. A61M 25/10 604/99.01 |

(Continued)

FOREIGN PATENT DOCUMENTS

| CN | 202459778 U | 10/2012 |
| WO | 2017158081 A1 | 9/2017 |
| WO | 2018234591 A1 | 12/2018 |

OTHER PUBLICATIONS

12 Crescent Examples in Real Life—StudiousGuy. https://studiousguy.com/crescent-examples/ Accessed Aug. 29, 2023.*

(Continued)

*Primary Examiner* — Adam Marcetich
(74) *Attorney, Agent, or Firm* — K&L Gates LLP

(57) ABSTRACT

The presently described catheter is an improved multi-function hypospadias catheter adapted to be urethrally inserted and secured within a patient's bladder using an attached internal crescent shaped retention balloon. The inverted crescent configuration of the balloon reduces the contact surface area between the balloon and a patient's bladder wall to reduce bladder spasms. The catheter is removed from the patient (when needed) via deflation of the crescent shaped balloon, which deflates completely so as to not contact a patient's urethra during insertion and removal of the catheter. The catheter includes a double lumen with a one-way flow valve. One lumen provides a passageway to drain urine from a patient's bladder. The second lumen provides a passageway to inflate and deflate the crescent shaped retention balloon.

20 Claims, 4 Drawing Sheets

(51) Int. Cl.
*A61M 25/10* (2013.01)
*A61M 39/00* (2006.01)

(52) U.S. Cl.
CPC ........ *A61M 25/04* (2013.01); *A61M 25/1002* (2013.01); *A61M 2025/0063* (2013.01); *A61M 2025/0078* (2013.01); *A61M 2039/0018* (2013.01); *A61M 2205/0266* (2013.01); *A61M 2210/1085* (2013.01)

(58) Field of Classification Search
CPC .... A61M 2025/1004; A61M 2025/105; A61M 2025/1065; A61M 2205/0266; A61M 2210/1085; A61M 25/00; A61M 25/0067; A61M 25/0074; A61M 25/0102; A61M 25/09025
See application file for complete search history.

(56) References Cited

U.S. PATENT DOCUMENTS

| | | | |
|---|---|---|---|
| 3,867,945 A | 2/1975 | Long | |
| 4,157,094 A * | 6/1979 | Patel | A61M 25/1034 604/98.01 |
| 4,177,815 A * | 12/1979 | Patel | A61M 25/1034 604/103 |
| 4,217,903 A | 8/1980 | Witherow | |
| 4,568,338 A * | 2/1986 | Todd | A61M 25/0041 604/530 |
| 4,686,985 A * | 8/1987 | Lottick | A61M 29/02 606/192 |
| 4,813,935 A | 3/1989 | Haber et al. | |
| 5,417,657 A | 5/1995 | Hauer | |
| 5,653,690 A * | 8/1997 | Booth | A61M 25/04 604/103.07 |
| 5,738,654 A * | 4/1998 | Tihon | A61F 2/04 604/105 |
| 5,769,818 A * | 6/1998 | El Maoued | A61M 25/10 604/103.03 |
| 6,283,940 B1 * | 9/2001 | Mulholland | A61M 25/0075 606/198 |
| 6,358,229 B1 * | 3/2002 | Tihon | A61M 25/0017 604/164.01 |
| 6,626,876 B1 * | 9/2003 | Bolmsjo | A61F 2/0022 604/525 |
| 2003/0176758 A1 * | 9/2003 | Nakano | A61M 25/1027 600/3 |
| 2004/0172009 A1 | 9/2004 | Marisi | |
| 2005/0159645 A1 * | 7/2005 | Bertolero | A61B 1/00142 600/116 |
| 2008/0071250 A1 * | 3/2008 | Crisp | A61M 25/0017 604/544 |
| 2009/0030370 A1 | 1/2009 | Nishtala et al. | |
| 2011/0098683 A1 * | 4/2011 | Wiita | A61M 25/0069 604/544 |
| 2011/0152842 A1 * | 6/2011 | Graffam | A61M 25/0052 604/540 |
| 2013/0331824 A1 | 12/2013 | Kim | |
| 2013/0338580 A1 | 12/2013 | Yamatani | |
| 2014/0012235 A1 * | 1/2014 | Pinchuk | A61M 25/10185 604/544 |
| 2015/0359996 A1 * | 12/2015 | Arora | A61M 25/0017 600/300 |
| 2018/0043135 A1 | 2/2018 | Chen et al. | |
| 2019/0091440 A1 * | 3/2019 | Lüning | A61M 25/10 |
| 2019/0240448 A1 * | 8/2019 | Murdock | A61M 25/0017 |

OTHER PUBLICATIONS

European Search Report for related European Application No. 19768669.4; action dated Dec. 1, 2021; (7 pages).
International Search Report for related International Application No. PCT/QA2019/050004; report dated Aug. 26, 2020; (2 pages).
Written Opinion for related International Application No. PCT/QA2019/050004; report dated Aug. 26, 2020; (6 pages).

* cited by examiner

MULTI-FUNCTION HYPOSPADIAS CATHETER

PRIORITY CLAIM

The present application is a National Phase of International Application No. PCT/QA2019/050004, filed Mar. 8, 2019 which claims priority to US Provisional Application No. 62/642,345 filed on Mar. 13, 2018, the entire contents of which are incorporated herein by reference and relied upon.

BACKGROUND

Hypospadias is a congenital disorder of the urethra where the urinary opening is not at the usual location on the head of the penis. Hypospadias is a common malformation with an incidence of about 1 per 300 male babies, although it differs in different populations between 0.3 and 7.0 per 1,000 live births. The tubular urethra proximal to the ectopic meatus is often hypoplastic, not surrounded by any corpus spongiosum and covered by a thin layer of skin tightly stuck on it. Proximally to the division of the corpus spongiosum, all structures forming the ventral aspect of the penis are "normal" as well as the dorsum.

Surgery is usually recommended for hypospadias, with the goal to restore normal appearance and function to the penis, such as extending the urinary channel to the end of the penis. Subjects recovering from such a surgery will often be discharged with a catheter to be used as the site of the surgery heals.

Traditional catheters are significantly vulnerable to being dislodged, particularly with the pediatric age group. Catheter dislodgement leads to health complications, including failure of the surgical repair. A currently used technique to prevent dislodgement and secure catheters in place is through suturing the catheter tube to the glans penis. This, however, can cause pain during removal and sometimes long-term visible, deep tracts in the glans penis. Another technique involves using an internal retention member, such as a retention balloon that inflates within a subject's urinary bladder and prevents the catheter from being dislodged.

Another problem with traditional catheters is that they cause discomfort and bladder spasms because parts of the catheter, such as a retention balloon, are present within the urinary bladder. Traditional catheters using retention balloons increase this discomfort and risk of spasms because the retention balloons currently being used contact the lining of a subject's urinary bladder over a large surface area.

Furthermore, most of the currently used catheters have balloons that remain corrugated outside the external diameter of the catheter after the balloon is deflated. This cannot only cause a subject pain during catheter removal, but can also damage a surgically repaired hypospadias as the balloon makes contact with the walls of the urethra.

Traditional catheters are also difficult to connect with urine collection bags and syringes and need different parts for connection and assembly with such bags. Further, in such traditional catheters, urine and other fluids can be sucked towards the bladder through the tube of the catheter due to transient negative pressure within the urinary bladder. Traditional catheters are also difficult to insert in severe hypospadias cases where there is frequently hypertrophied utricle.

Additionally, because the human body considers all catheter components to be foreign bodies, their presence in the body results in a high rate of urinary tract infections. Urinary tract infections ("UTI's") are considered the most common hospital acquired infections and account for about 40% of infections. About 80% of all UTI's acquired during hospital stays are caused by urinary catheters. Some of the currently available catheter tubes are also easily kinkable and can obstruct the flow of urine, causing pain and increasing the risk of UTI's.

The presently described catheter system seeks to address the above described problems. The disclosure also aims to address other objects and solutions that appear in greater detail below.

BRIEF SUMMARY OF THE INVENTION

The presently described catheter is an improved multi-function hypospadias catheter adapted to be urethrally inserted and secured within a pediatric or adult patient via an attached crescent shaped balloon and removed from the patient (when needed) via deflation of the balloon. The crescent shaped balloon contacts a subject's bladder significantly less than traditional catheters and results in less discomfort and bladder spasms.

In light of the disclosures herein, and without limiting the scope of the invention in any way, in a first aspect of the present disclosure, which may be combined with any other aspect listed herein unless specified otherwise, a hypospadias catheter device comprises a dual lumen, a drainage channel, an inflation/deflation channel, and a crescent shaped retention balloon. The dual lumen comprises a first lumen and a second lumen. The drainage channel and inflation/deflation channel are located at the proximal end of the dual lumen. The drainage channel is coupled to the first lumen and the inflation/deflation channel is coupled to the second lumen. The crescent shaped retention balloon is in fluid communication with the second lumen and resides fully within the dual lumen when the balloon is in a deflated state.

In a second aspect of the present disclosure, which may be combined with any other aspect listed herein unless specified otherwise, the catheter device is further coated with a hydrophilic coating.

In a third aspect of the present disclosure, which may be combined with any other aspect listed herein unless specified otherwise, the dual lumen is bent at an angulation joint while the device is inserted within a patient and the dual lumen is straightened at the angulation joint during removal of the device. The angulation joint is located near a distal end of the dual lumen.

In a fourth aspect of the present disclosure, which may be combined with any other aspect listed herein unless specified otherwise, the crescent shaped retention balloon is inflated by fluid through the inflation/deflation channel and the second lumen.

In a fifth aspect of the present disclosure, which may be combined with any other aspect listed herein unless specified otherwise, the crescent shaped retention balloon is deflated by aspirating fluid from the balloon through the second lumen and the inflation/deflation channel.

In a sixth aspect of the present disclosure, which may be combined with any other aspect listed herein unless specified otherwise, the catheter device further includes an external self-flushing system.

In a seventh aspect of the present disclosure, which may be combined with any other aspect listed herein unless specified otherwise, the catheter device further comprises a mandrel that, when retracted, allows the double lumen to angulate, but when deployed, straightens the double lumen.

In an eighth aspect of the present disclosure, which may be combined with any other aspect listed herein unless specified otherwise, the catheter device further includes a one-way flow valve that allows urine to flow through the first lumen toward the proximal end of the dual lumen, but not towards the distal end of the dual lumen.

In a ninth aspect of the present disclosure, which may be combined with any other aspect listed herein unless specified otherwise, a method of securing a catheter device within a subject includes inserting a first end of a catheter device through a urethra of a subject until the device reaches a urinary bladder of the subject. The catheter device includes a dual lumen, a drainage channel, an inflation/deflation channel, and a crescent shaped retention balloon. The dual lumen includes a first lumen and a second lumen. The drainage channel is coupled to the first lumen and the inflation/deflation channel is coupled to the second lumen. The crescent shaped retention balloon is in fluid communication with the second lumen and resides fully within the dual lumen when the balloon is deflated. Once the crescent shaped balloon is within the urinary bladder of the subject, the method includes inflating the balloon.

In a tenth aspect of the present disclosure, which may be combined with any other aspect listed herein unless specified otherwise, the method further comprises aspirating fluid from the crescent shaped retention balloon through the second lumen and the inflation/deflation channel until the balloon is in a deflated state.

In an eleventh aspect of the present disclosure, which may be combined with any other aspect listed herein unless specified otherwise, the crescent shaped retention balloon resides fully within the dual lumen when the balloon is in a deflated state.

In a twelfth aspect of the present disclosure, which may be combined with any other aspect listed herein unless specified otherwise, the crescent shaped retention balloon is inflated with fluid through the inflation/deflation channel and the second lumen.

In a thirteenth aspect of the present disclosure, which may be combined with any other aspect listed herein unless specified otherwise, the catheter device used in the method is further coated with a hydrophilic coating.

In a fourteenth aspect of the present disclosure, which may be combined with any other aspect listed herein unless specified otherwise, the dual lumen of the catheter device used in the method is bent at an angulation joint while the device is inserted within the subject and the dual lumen is straightened at the angulation joint during removal of the device. The angulation joint is located near a distal end of the dual lumen.

In a fifteenth aspect of the present disclosure, which may be combined with any other aspect listed herein unless specified otherwise, the catheter device used in the method further includes an external self-flushing system.

In a sixteenth aspect of the present disclosure, which may be combined with any other aspect listed herein unless specified otherwise, the catheter device further comprises a mandrel that, when retracted, allows the double lumen to angulate, but when deployed, straightens the double lumen.

In a seventeenth aspect of the present disclosure, which may be combined with any other aspect listed herein unless specified otherwise, the catheter device used in the method further includes a one-way flow valve that allows urine to flow through the first lumen toward the proximal end of the dual lumen, but not towards the distal end of the dual lumen.

DETAILED DESCRIPTION

Figure 1A:
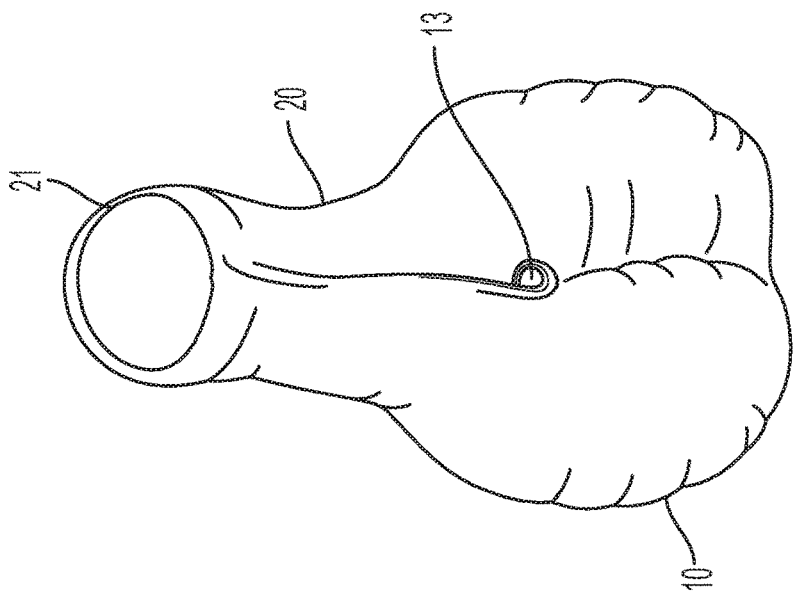
FIGS. 1A, 1B, and 1C illustrate the different types of hypospadias in male subjects.
Figure 1B:
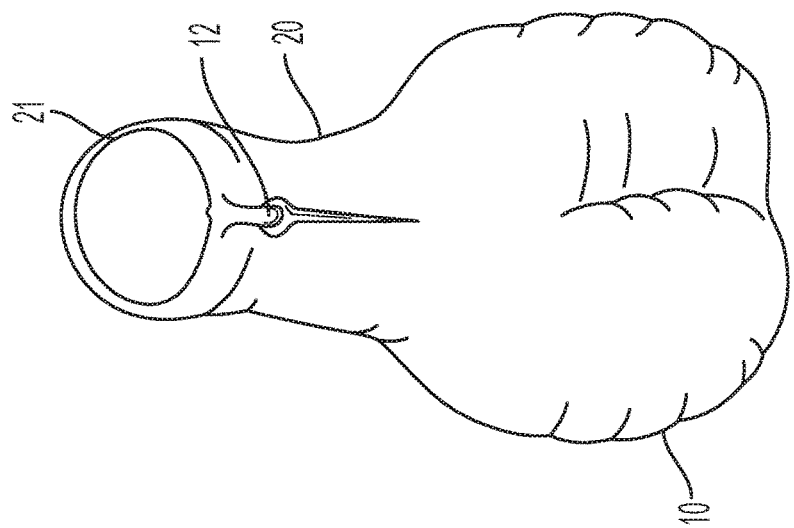
Figure 1C:
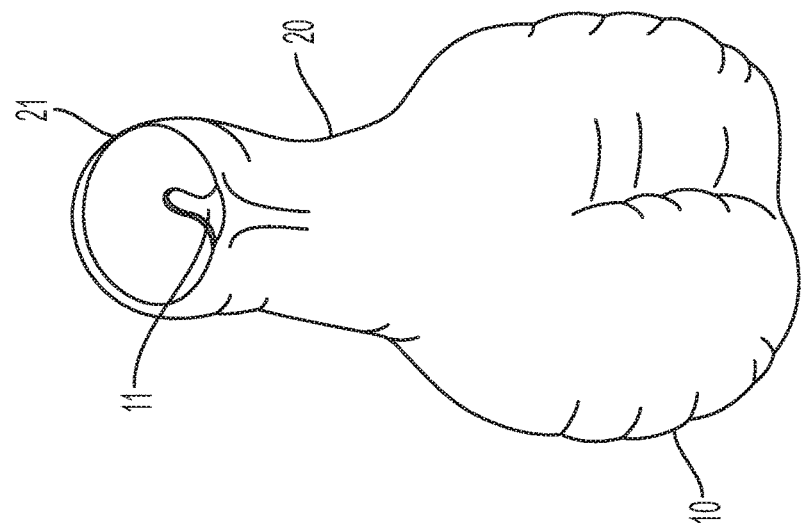

Hypospadias is a congenital disorder of the urethra where the urinary opening is not at the usual location on the head of the penis. Different types of this disorder are illustrated in FIGS. 1A-1C with the urinary opening at different locations. FIG. 1A illustrates a scrotum 10, a penis 20, a glans penis 21, and a subcoronal urinary opening 11. FIG. 1B illustrates a midshaft urinary opening 12, and FIG. 1C illustrates a penoscrotal urinary opening 13.

Hypospadias is a common malformation with an incidence of about 1 per 300 male babies, although it differs in different populations between 0.3 and 7.0 per 1,000 live births. Surgery is usually recommended for hypospadias, with the goal to restore normal appearance and function to the penis, such as extending the urinary channel to its usual location, the end of the penis. Subjects recovering from such a surgery will often be discharged with a catheter to be used as the site of the surgery heals.

The presently disclosed catheter provides many benefits to patients undergoing and recovering from hypospadias surgery. For example, the disclosed catheter comprises a crescent shaped retention balloon that contacts a patient's bladder significantly less than current catheters, and thus causes less discomfort and bladder spasms. The catheter also reduces the incidence of infections associated with catheters post hypospadias surgery. This may be accomplished by using one or more hydrophilic coatings, a one-way valve that prevents back flow of urine inwards, and/or by using closed system urine collection bags.

Figure 2:
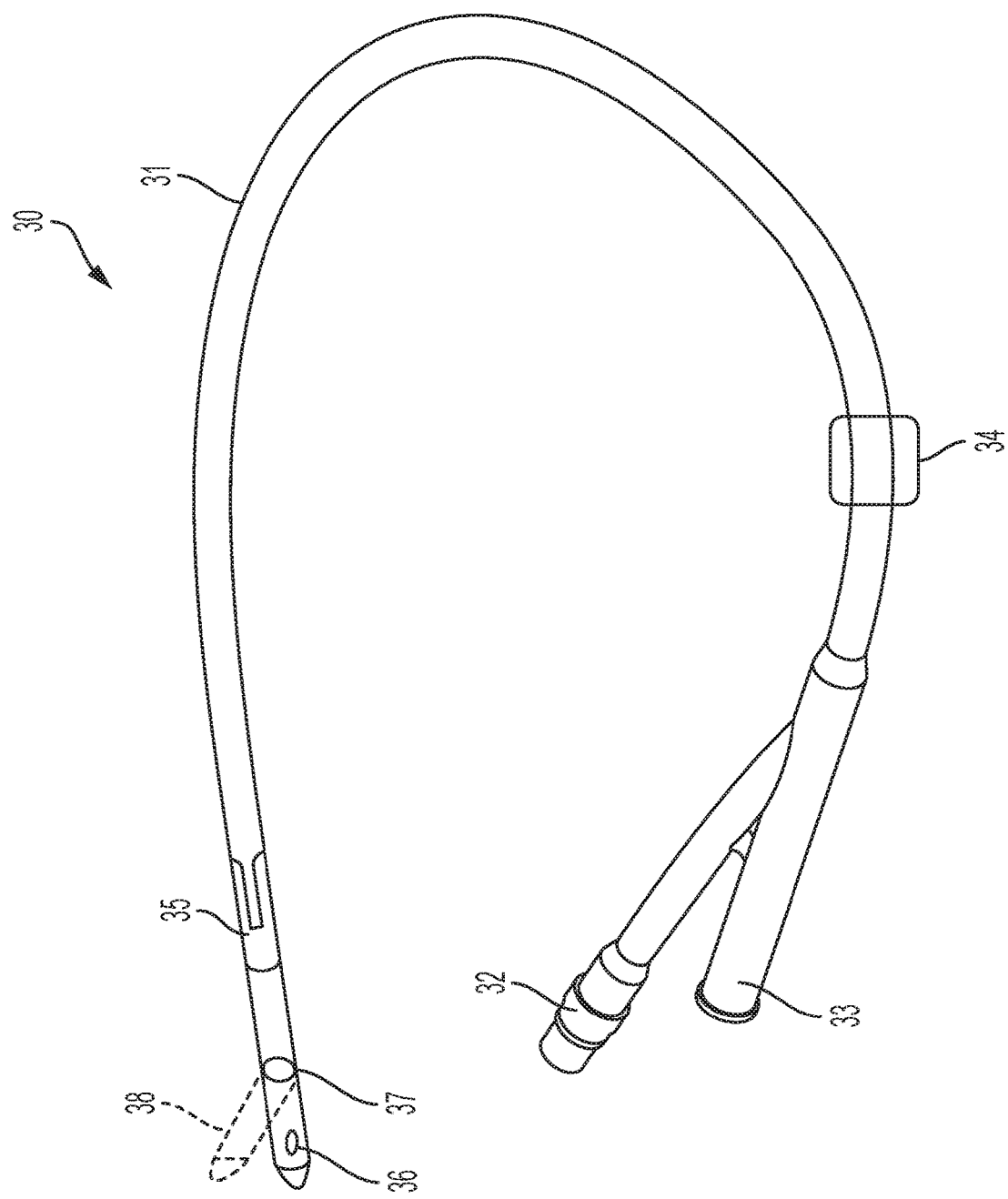
FIG. 2 illustrates the presently disclosed hypospadias catheter.

Referring now to FIG. 2, a hypospadias catheter 30 comprises a double lumen 31 with two lumen openings located at a proximal end of the double lumen 31. In one embodiment, the two lumen openings form a V-shaped portion at the end of the double lumen 31 as illustrated. A urine channel 36 is located at a distal end of the double lumen 31. When the catheter 30 is placed within a subject 40 (FIG. 3), the urine channel 36 is located within the bladder of the subject 40. As a result, urine flows into the urine channel 36 and through a single lumen providing a passageway to the drainage channel 33, the first lumen opening. In the illustrated embodiment, the urine channel 36 is shown as a small slit near the distal tip of the double lumen 31. In other embodiments, the urine channel 36 can have other shapes, screen filters, perforations, or design features, as desired, to provide fluid passage as easily as possible.

The second lumen opening, the inflation/deflation channel 32, provides a passageway, by way of a second lumen, to the crescent shaped retention balloon 35. In one embodiment, the crescent shaped balloon 35 is inflated once it reaches a subject's bladder by fluid insufflation through the inflation/deflation channel 32 and the second lumen. In such an embodiment, when it is time for the catheter 30 to be removed, the balloon 35 is deflated by aspirating the fluid from the balloon 35 through the inflation/deflation channel 32 and the second lumen. In other embodiments, the balloon 35 may be inflated or deflated by other means, such as air.

The balloon 35 is shown in an embodiment of a deflated state in FIG. 2 to illustrate one of the benefits of the presently disclosed catheter 30. Most of the currently used catheters have balloons that remain corrugated outside the external diameter of the catheter after deflation and thus cause pain during their removal, or cause damage to a surgically repaired hypospadias. The crescent shaped balloon 35 in a deflated state, on the other hand, is completely collapsible within the double lumen 31 of the catheter 30 such that no external protrusions of the deflated balloon 35 are felt outside the outer diameter of the double lumen 31. For example, the balloon 35 does not contact the walls of the urethra as the catheter 30 is inserted or removed from a subject. In one embodiment, this can be accomplished by maintaining a less deformable (high shape memory) external layer at the level of the balloon 35 that is continuous with the external surface of the double lumen 31 both before and after the region of the balloon 35. This aspect of the present disclosure provides the benefit of preventing any injury or friction to the urethra or damage to the urethral repair when removing the catheter 30 post-operation.

It should be appreciated that in various embodiments, the passages in the double lumen 31 are parallel passages within the double lumen 31 and in various other embodiments, the passages are coaxial. In either case the urine carrying passage extends beyond the passage for inflating/deflating and housing the balloon 35. In other words, the distal end of the double lumen structure has a distal tip that defines a single lumen. In either case, the angulation joint 37 discussed below would be defined near the point where the urine carrying passage extends beyond the passage for inflating/deflating and housing the balloon 35.

In severe hypospadias cases, traditional catheters are often difficult to insert because there is frequently hypertrophied utricle. To overcome this problem, the presently disclosed catheter 30 includes an angulation joint 37 which provides for transient angulation of the double lumen 31 near the end where the catheter 30 is inserted into a subject (i.e., the distal end). The angulation joint 37 allows the distal end of the double lumen 31 to be at an angle to the rest of the double lumen 31, such as curved distal end 38 in FIG. 2, when the catheter is inserted into, or removed from, a subject. The angle can make it easier to insert the catheter in severe hypospadias cases.

In one embodiment, the distal end of the double lumen 31 (e.g., from the angulation joint 37 to the distal tip of the double lumen 31) is produced of a more flexible material than the rest of the double lumen 31, which is produced from a single malleable material. The soft, flexible material is more comfortable for a subject. The difference in material flexibility on either side of the angulation joint 37 allows the double lumen 31 to angulate at the angulation joint 37, such as curved distal end 38. In another embodiment, the distal end of the double lumen 31 is produced of a harder or less malleable material than the rest of the double lumen 31 to provide for the curved distal end 38. In another embodiment still, the entire double lumen 31 is produced of a single, malleable material.

The angulation joint 37 also allows the distal end of the double lumen 31 to be straightened completely, for example, during removal of catheter 30 to prevent pain or injuring the structure line of the hypospadias surgery area, as discussed above in relation to balloon 35. The double lumen 31 may also need to be straightened completely during insertion of the catheter 30 as well. In one embodiment, the catheter 30 includes or is operable with a mandrel that, when withdrawn towards the proximal end of the double lumen 31, allows the double lumen 31 to angulate at the angulation joint 37, but when deployed into the distal end of the double lumen 31, prevents the double lumen 31 from angulation and keeps it straight. In other embodiments, the distal end of the double lumen 31 may be straightened using other means. Thus, the double lumen 31 can be freely angulated or straightened as needed.

In relation to the above discussed angulation, some prior art catheters include tubes, such as double lumens, that can easily be kinked. Thus, if some prior art catheters utilized the presently disclosed angulation joint, the tube may kink and obstruct the flow of urine, which causes pain and increases the risk of the subject developing a UTI. The presently claimed catheter 30, however, includes a double lumen 31 composed of a material that cannot be kinked due to its mechanical characteristics. In this regard, the mechanical properties of the double lumen 31 can be manipulated to provide a desired patency of the catheter device 30 regardless of the degree of angulation. In this regard, the catheter may have a patency of 50% or greater, preferably 70% or greater, even more preferably 80% or greater, even more preferably 90% or greater and most preferably 95% or greater.

Similar to the kinking problem in traditional catheters, urine and other fluids can be sucked towards the urinary bladder through a traditional catheter due to transient negative pressure within the urinary bladder. This can also cause patients to contract UTI's. The presently disclosed catheter 30 mitigates this problem by including a one-way valve 34 that permits the flow of urine from within the patient to external to the patient through the catheter 30, but prevents the flow of urine from external to the patient to internal to the patient.

Additionally, catheters are a leading cause of UTI's because the body considers them to be foreign bodies. In at least one embodiment, the presently disclosed catheter 30 is coated with a hydrophilic coating with anti-infection properties to combat a subject's risk for a UTI. Hydrophilic coatings have been well explored as catheter coating alternatives due to their hydrophilic properties, which act as a deterrent to hydrophobic bacterial surfaces and encrusting deposits within the urine. In at least one embodiment, the catheter 30 is coated with polyethylene glycol (PEG). PEG is a commonly used hydrophilic coating due to its success as an antifouling agent, a result of its high degree of mobility and steric hindrance in chemical structure. The structure of this polyether allows it to couple numerous water molecules reducing its coefficient of friction and driving its fluid like behavior. In various other embodiments, catheter 30 is coated with a hydrophilic coating other than PEG.

Figure 3:
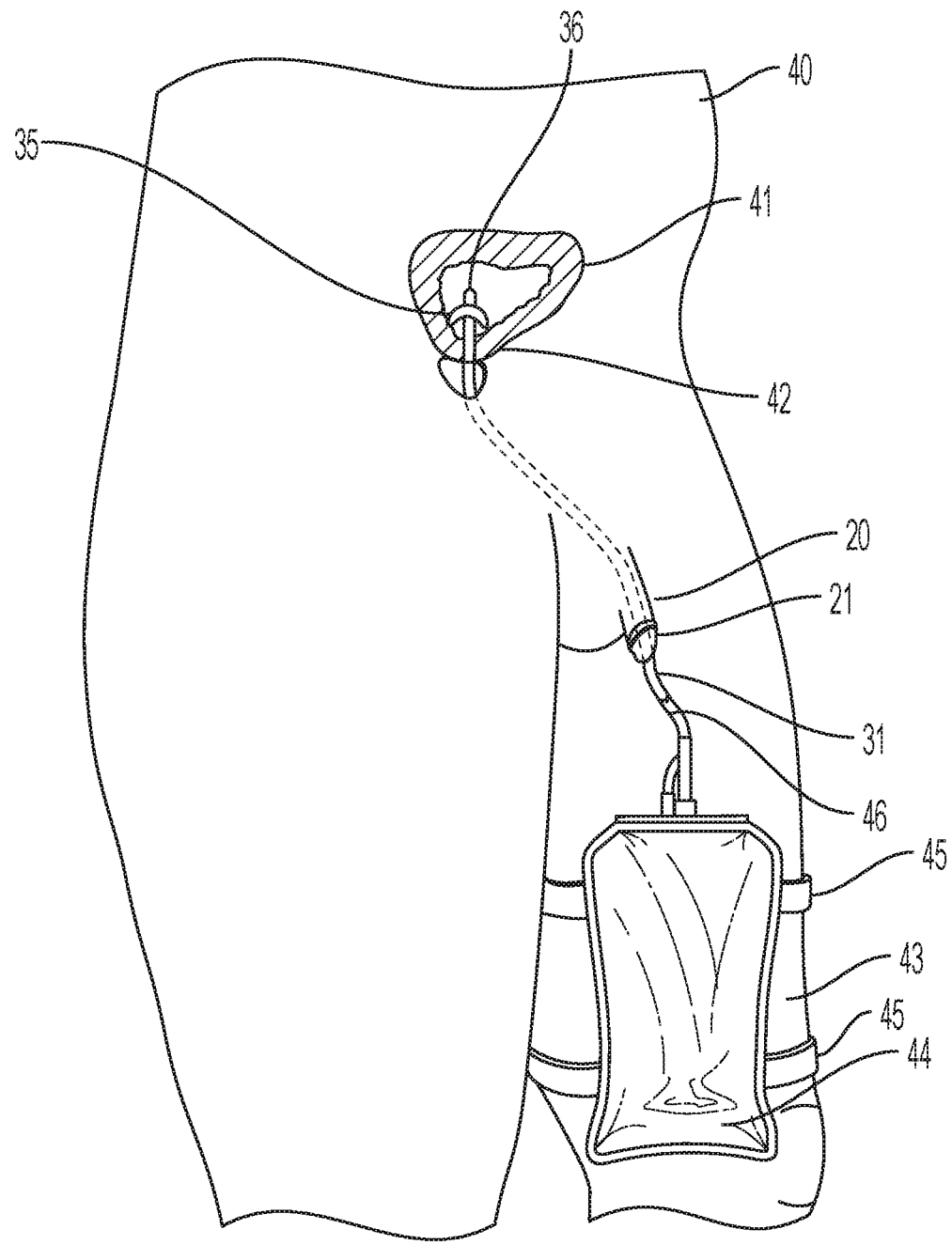
FIG. 3 illustrates the presently disclosed hypospadias catheter inserted within an example pediatric subject and attached to a urine collector bag.

Referring now to FIG. 3, an example pediatric subject 40 is illustrated wearing the presently disclosed catheter 30. The distal tip of double lumen 31 of the catheter 30 is inserted through the urethral opening at glans penis 21 until the distal tip reaches bladder 41. The urine channel 36 is shown in bladder 41 and the crescent shaped retention balloon 35 is inflated, securing the catheter 30 within the bladder 41. In the illustrated embodiment, the double lumen 31 is shown within the urethra of pediatric subject 40 and attached to urine collector bag 44 external to pediatric subject 40. In other embodiments, urine collection means may be used other than a urine collector bag 44, or a collection means may not be used at all. For example, the urine may be allowed to flow directly into a diaper. One advantage, however, of utilizing a collection means is decreasing the potential chances of bacterial migration and a UTI. In the illustrated embodiment, the urine collector bag 44 is also shown secured to the thigh 43 of pediatric subject 40 with urine collector bag straps 45. In other embodiments that utilize a collection means, securing means other than straps 45 may be used.

Additionally, traditional catheters are often difficult to connect with urine collection bags and syringes and need different parts for connection and assembly with such bags. The external component of the double lumen 31 of the presently disclosed catheter 30 can easily be connected to bags and syringes without the need for the use of adapters. In one embodiment, the external component of the catheter 30 is similar to that of a standard Foleys catheter (which is used for routine urethral catheterization but not for hypospadias surgery).

In one embodiment, as illustrated, the presently disclosed catheter 30 additionally includes an external flushing system 46. The flushing system 46 flushes catheter 30 by creating a rapid negative pressure by sucking a burst of surrounding air into the lumen that leads to urine channel 36. This rapid negative pressure will clear any obstruction in the lumen (e.g., blood clot or small foreign body) and allow the urine to flow freely. In one embodiment, a subject 40, or nurse or other helper, presses a button to activate the external flushing system 46. The button may physically depress and/or make a sound to provide auditory and tactile feedback to the subject that the flushing system 46 is working as expected. In other embodiments, the flushing system 46 may be activated by means other than a button or may give other indications to the user that it is working properly. In other embodiments still, the flushing system 46 may not give the user an indication that it is working other than its normal flushing function.

Figure 4A:
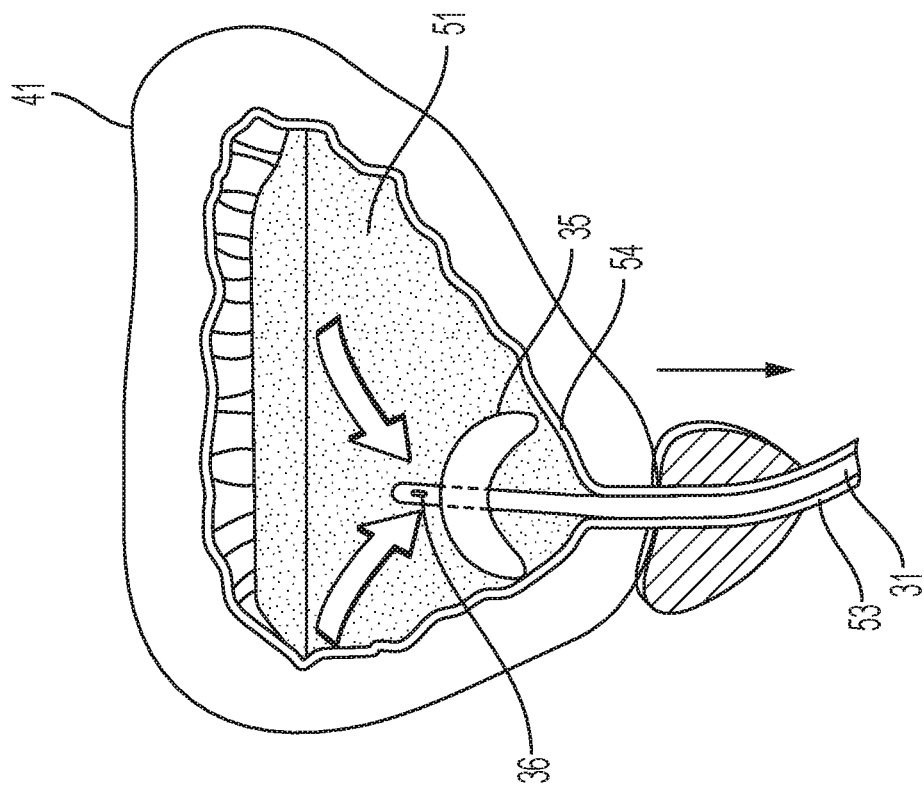
FIGS. 4A and 4B illustrate a catheter with a sphere shaped retention balloon placed within a urinary bladder as compared to the presently disclosed catheter with a crescent shaped retention balloon.
Figure 4B:
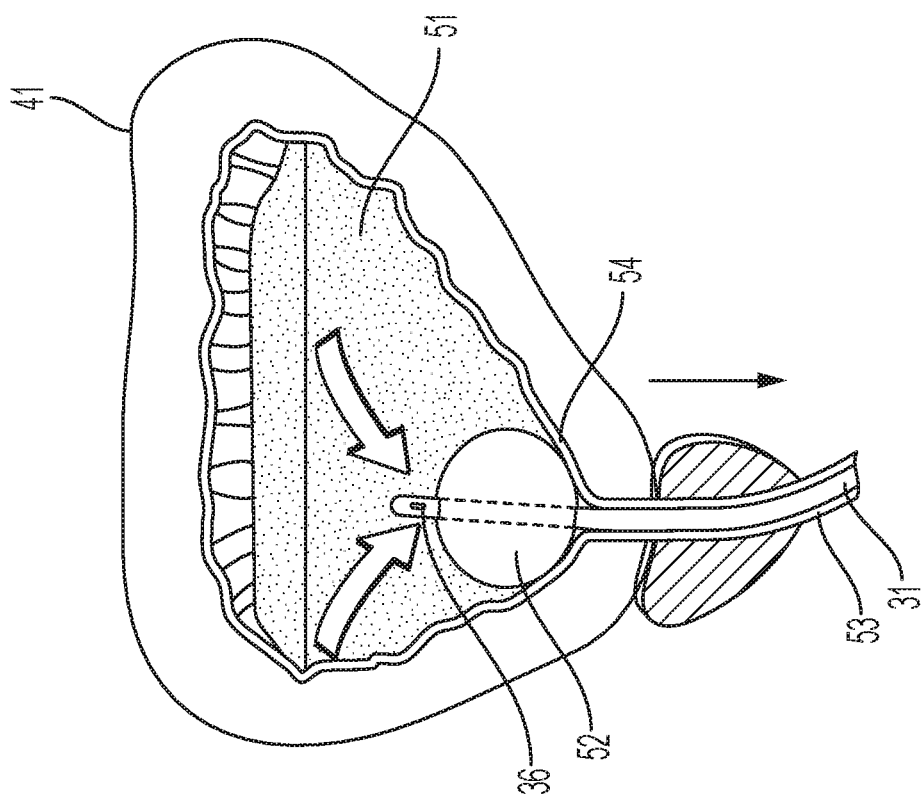

Now referring to FIG. 4, a prior art catheter with a sphere shaped retention balloon 52 is illustrated in FIG. 4A in comparison to the presently disclosed catheter 30 with a crescent shaped retention balloon 35 in FIG. 4B. The catheter in FIG. 4A is shown secured within bladder 41 by the sphere shaped balloon 52. Urine 51 flows into the urine channel 36 and down (in the direction of the arrow) one lumen of double lumen 31 which is within urethra 53.

Traditional catheters such as the one illustrated in FIG. 4A cause discomfort and bladder spasms because of the large contact surface area between the sphere shaped retention balloon 52 and a subject's bladder wall 54. Complications from these traditional catheters include loin pain in 21.6% of patients and irrigative symptoms in 30.5% of patients. The presently disclosed catheter 30 illustrated in FIG. 4B, on the other hand, includes a retention balloon 35 having an inverted crescent configuration that reduces the contact surface area between the balloon 35 and a subject's bladder wall 54. The reduction in surface area contact is illustrated in comparing FIGS. 4A and 4B, and can be as great as 90% as compared to a traditional catheter. This reduction in contact surface area decreases the risk and discomfort associated with postoperative bladder spasms and the need to prescribe anticholinergics with its several side effects.

When the presently disclosed catheter 30 needs to be removed, the crescent shaped retention balloon 35 collapses completely after deflation without extending beyond the limits of the external diameter of the double lumen 31. The catheter 30 can then be pulled out of the bladder 41 through the urethra 53 without external protrusions contacting the walls of the urethra 53.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated.

The invention is claimed as follows:

1. A catheter device comprising:
   a dual lumen, wherein the dual lumen comprises a first lumen and a second lumen;
   a drainage channel at a proximal end of the dual lumen, the drainage channel coupled to the first lumen;
   an inflation/deflation channel at the proximal end of the dual lumen, the inflation/deflation channel coupled to the second lumen; and
   a crescent shaped retention balloon, wherein the crescent shaped retention balloon is in fluid communication with the second lumen and resides fully within the dual lumen when the crescent shaped retention balloon is in a deflated state and, when the crescent shaped retention balloon is in an expanded state, arcuately projects outward from the second lumen via a first arm and a second arm that curve towards the proximal end and are held out of contact from the dual lumen.

2. The catheter device of claim 1, wherein the catheter device is further coated with a hydrophilic coating.

3. The catheter device of claim 1, wherein the dual lumen includes an angulation joint near a distal end of the dual lumen, and wherein the angulation joint is configured such that the dual lumen may be straight or bent at an angle at the angulation joint.

4. The catheter device of claim 1, wherein the crescent shaped retention balloon is configured to be inflated by fluid introduced through the inflation/deflation channel and the second lumen.

5. The catheter device of claim 1, wherein the crescent shaped retention balloon is configured to be deflated upon fluid being aspirated from the crescent shaped retention balloon through the second lumen and the inflation/deflation channel.

6. The catheter device of claim 1, wherein the catheter device further comprises an external self-flushing system.

7. The catheter device of claim 1, wherein the catheter device further comprises a mandrel that, when retracted, allows the double lumen to angulate, but when deployed, straightens the double lumen.

8. The catheter device of claim 1, wherein the catheter device further comprises a one-way flow valve configured to permit the flow of urine through the first lumen towards the proximal end of the dual lumen, but to prevent the flow of urine towards the distal end of the dual lumen.

9. The catheter device of claim 1, wherein an external surface of the dual lumen includes a shape memory material layer at a position of the dual lumen at which the crescent shaped retention balloon expands out of the dual lumen to the expanded state.

10. The catheter device of claim 1, wherein the crescent shaped retention balloon is positioned on the distal end of the dual lumen relative to the drainage channel at the proximal end of the dual lumen.

11. A method of securing a catheter device within a subject comprising the steps of:

inserting a first end of a catheter device through a urethra of a subject until the device reaches a urinary bladder of the subject, the catheter device comprising:
    a dual lumen, wherein the dual lumen comprises a first lumen and a second lumen;
    a drainage channel at a proximal end of the dual lumen, the drainage channel coupled to the first lumen;
    an inflation/deflation channel at the proximal end of the dual lumen, the inflation/deflation channel coupled to the second lumen; and
    a crescent shaped retention balloon, wherein the crescent shaped retention balloon is in fluid communication with the second lumen and resides fully within the dual lumen when the crescent shaped retention balloon is in a deflated and, when the crescent shaped retention balloon is in an inflated state, arcuately projects outward from the second lumen via a first arm and a second arm that curve towards the proximal end and are held out of contact from the dual lumen; and
inflating the crescent shaped retention balloon via the inflation/deflation channel and the second lumen when the crescent shaped retention balloon is within the urinary bladder of the subject, wherein distal tips of the first arm and the second arm of the crescent shaped retention balloon contact the urinary bladder and other portions of the crescent shaped retention balloon and held out of contact with the urinary bladder.

12. The method of claim 11, wherein the method further comprises aspirating fluid from the crescent shaped retention balloon through the second lumen and the inflation/deflation channel until the balloon is in a deflated state.

13. The method of claim 12, wherein the crescent shaped retention balloon resides fully within the dual lumen when the balloon is in a deflated state.

14. The method of claim 11, wherein the crescent shaped retention balloon is inflated by introducing fluid through the inflation/deflation channel and the second lumen into the crescent shaped retention balloon.

15. The method of claim 11, wherein the catheter device is further coated with a hydrophilic coating.

16. The method of claim 11, wherein the dual lumen is bent at an angulation joint while the catheter device is inserted within a subject, the angulation joint being located near a distal end of the dual lumen, and the dual lumen is straightened at the angulation joint during removal of the catheter device.

17. The method of claim 11, wherein the catheter device further comprises an external self-flushing system.

18. The method of claim 11, wherein the catheter device further comprises a mandrel that, when retracted, allows the double lumen to angulate, but when deployed, straightens the double lumen.

19. The method of claim 11, wherein the catheter device further comprises a one-way flow valve configured to permit the flow of urine through the first lumen towards the proximal end of the dual lumen, but to prevent the flow of urine towards the distal end of the dual lumen.

20. The method of claim 11, wherein the crescent shaped retention balloon includes a first surface defining a first arc between the distal ends of the first arm and the second arm and a second surface defining a second arc between the distal ends of the first arm and the second arm.

* * * * *